(12) United States Patent
Hlavinka et al.

(10) Patent No.: US 8,048,055 B2
(45) Date of Patent: Nov. 1, 2011

(54) CLAMP ASSEMBLY FOR DISPLACING FLUID FROM PORTIONS OF FLUID CONTAINERS

(75) Inventors: Dennis J. Hlavinka, Arvada, CO (US); Terrence M. Cussen, Englewood, CO (US)

(73) Assignee: CaridianBCT Biotechnologies, LLC, Lakewood, CO (US)

( * ) Notice: Subject to any disclaimer, the term of this patent is extended or adjusted under 35 U.S.C. 154(b) by 306 days.

(21) Appl. No.: 12/548,656

(22) Filed: Aug. 27, 2009

(65) Prior Publication Data

US 2009/0317296 A1    Dec. 24, 2009

Related U.S. Application Data

(62) Division of application No. 11/268,077, filed on Nov. 7, 2005, now abandoned.

(51) Int. Cl.
*A61M 19/00* (2006.01)
*A61M 37/00* (2006.01)
*B65D 33/00* (2006.01)

(52) U.S. Cl. ....... 604/408; 604/6.1; 604/6.08; 604/6.16; 383/210.1

(58) Field of Classification Search .............. 422/44; 604/6.08, 6.09, 140; 251/9; 269/20, 22, 269/32, 24; 417/474, 477.9; 383/210.1
See application file for complete search history.

(56) References Cited

U.S. PATENT DOCUMENTS

| | | | |
|---|---|---|---|
| 4,469,227 A | 9/1984 | Faust | |
| 4,726,949 A | 2/1988 | Miripol et al. | |
| 4,830,510 A | 5/1989 | Bellhouse | |
| 4,866,282 A | 9/1989 | Miripol et al. | |
| 4,878,896 A | 11/1989 | Garrison et al. | |
| 4,952,812 A | 8/1990 | Miripol et al. | |
| 5,496,301 A | 3/1996 | Hlavinka et al. | |
| 5,547,108 A * | 8/1996 | Gsell et al. | 222/95 |
| 5,685,875 A | 11/1997 | Hlavinka et al. | |
| 5,866,074 A | 2/1999 | Chapman et al. | |

(Continued)

FOREIGN PATENT DOCUMENTS

EP    0610778    8/1994

(Continued)

OTHER PUBLICATIONS

International Search Report for PCT/US2006/042934, Jun. 3, 2007.

*Primary Examiner* — Leslie Deak
(74) *Attorney, Agent, or Firm* — Edna M. O'Connor; John R. Merkling; Laura Butterfield Arciniegas

(57) ABSTRACT

Clamps and methods are disclosed for clamping portions of fluid containers and displacing fluid from portions of fluid containers. In one embodiment, a clamp has a first jaw having a photopermeable main body portion and a second jaw. The first and second jaws are operatively associated so that at least one jaw, or both jaws, may be moved between clamped and released positions. The clamp is sized to receive a portion of a fluid container and displace fluid in the fluid container from a clamped region of the fluid container when the first and/or second jaw(s) are in the clamped position. The photopermeable main body portion(s) of the first and/or second jaw(s) allow some light to reach the clamped region of the fluid container during photoradiation to inactivate pathogens in the fluid. Various clamp embodiments and assemblies having lock members and interlocks are also disclosed herein.

17 Claims, 11 Drawing Sheets

U.S. PATENT DOCUMENTS

| | | |
|---|---|---|
| 5,965,349 A | 10/1999 | Lin et al. |
| 6,158,319 A | 12/2000 | D'Silva |
| 6,245,570 B1 | 6/2001 | Grimm et al. |
| 6,258,577 B1 | 7/2001 | Goodrich, Jr. et al. |
| 6,277,337 B1 | 8/2001 | Goodrich, Jr. et al. |
| 6,369,394 B1 | 4/2002 | Lee |
| 6,548,241 B1 | 4/2003 | McBurney et al. |
| 6,565,802 B1 | 5/2003 | Hanley et al. |
| 6,696,023 B2 | 2/2004 | Grimm et al. |
| 6,740,239 B2 | 5/2004 | Hogberg et al. |
| 6,843,961 B2 | 1/2005 | Hlavinka et al. |
| 6,869,653 B2 | 3/2005 | Ling et al. |
| 6,902,539 B2 | 6/2005 | Bainbridge et al. |
| 7,094,378 B1 | 8/2006 | Goodrich et al. |
| 7,780,644 B2 * | 8/2010 | Miyajima et al. .............. 604/408 |
| 2002/0043051 A1 | 4/2002 | Manica et al. |
| 2004/0186412 A1 | 9/2004 | Mallett et al. |

FOREIGN PATENT DOCUMENTS

| | | |
|---|---|---|
| JP | 05146484 | 6/1993 |
| WO | WO 98/22164 | 5/1998 |
| WO | WO03/082181 | 10/2003 |
| WO | WO 03/086479 | 10/2003 |
| WO | WO2004/047714 | 6/2004 |

* cited by examiner

CLAMP ASSEMBLY FOR DISPLACING FLUID FROM PORTIONS OF FLUID CONTAINERS

PRIORITY

This application is a divisional of U.S. patent application Ser. No. 11/268,077 filed on Nov. 7, 2005.

BACKGROUND

Contamination of blood and blood components with infectious microorganisms or pathogens creates a serious risk for patients who receive blood or blood components via blood transfusions. Infectious microorganisms or pathogens, include, but are not limited to, viruses, bacteria, bacteriophages, fungi, blood transmitted parasites, and protozoa. Examples of transfusable blood or blood components may include whole blood, packed red blood cells, white blood cells, platelets, and plasma, just to name a few. To combat the contamination problem, blood and blood components can be decontaminated using pathogen inactivating agents or photosensitizers which, when activated, inactivate pathogens within the blood or blood components without destroying the biological activity of the blood or blood components.

Pathogen inactivation agents which may be useful for decontamination include the class of photosensitizers known in the art to be useful for inactivating microorganisms. U.S. Pat. No. 6,277,337 discloses a method and apparatus for inactivation of biological contaminants using photosensitizers and is also hereby incorporated by reference for all that it discloses.

A "photosensitizer" may be defined as any compound which absorbs radiation of one or more defined wavelengths and subsequently transfers the absorbed energy to an energy acceptor. Such photosensitizers may be activated by the application of electromagnetic spectra (e.g. light or photoradiation) to inactivate pathogens with which they may interact. Additionally, U.S. Pat. No. 6,258,577 discloses a method and apparatus for inactivation of biological contaminants using endogenous alloxazine or isoalloxazine photosensitizers and is hereby incorporated by reference for all that it discloses.

Decontaminating blood or blood components may be done by mixing an effective amount of a photosensitizer with the fluid to be decontaminated and then exposing the fluid to an amount of photoradiation at an appropriate wavelength sufficient to activate the photosensitizer and allowing the activated photosensitizer to inactivate at least some of the pathogens contained within the fluid. The wavelength of light used may depend on the photosensitizing agent selected. The light source(s) may provide light in the visible range, the ultraviolet range, or a mixture of light in both the visable and ultraviolet ranges. U.S. Pat. No. 6,843,961 discloses the reduction of contaminants in blood and blood products using photosensitizers and peak wavelengths of light and is hereby incorporated by reference for all that it discloses.

The fluid to be decontaminated may be flowed through an entry port into a photopermeable bag or fluid container. The term "photopermeable" means that the material of the container is adequately transparent to photoradiation of the proper wavelength for activating the photosensitizer. The fluid containers may contain a number of ports which provide access to the interior of the container. Such ports are typically manufactured, at least in part, out of polymeric materials, which are usually more rigid than the main body portion of the fluid container.

During pathogen inactivation, a portion of the fluid to be inactivated may become trapped or remain within one or more of these ports. One problem with these ports is that they may be constructed from a different material, or of the same material having a different thickness, than the main body portion of the fluid container, resulting in varying thicknesses for photopermeability. Another problem with these ports is that they may contain a larger volume of fluid than can be inactivated by a given exposure to the photoradiation. Consequently, fluids trapped within these port paths during pathogen inactivation may still contain infectious pathogens after the inactivation process is completed. These infectious pathogens may then reenter the otherwise decontaminated fluid, recontaminating the fluid.

SUMMARY OF THE INVENTION

One embodiment of a clamp includes a first jaw and a second jaw. The first jaw comprises a photopermeable main body portion. The second jaw is operatively associated with the first jaw so that at least one of the first and second jaws can be moved between a clamped position and a released position. The clamp is sized to receive a portion of a fluid container. The clamp displaces fluid in the fluid container from a clamped region of the fluid container when the first and second jaws are in the clamped position. The photopermeable main body portion of the first jaw allows some wavelengths of light to reach the clamped region of the fluid container.

Also disclosed is a method which includes: positioning a portion of a fluid container containing a fluid adjacent to a photopermeable main body portion of a displacement device; using the displacement device to apply a displacing force to a portion of the fluid container to displace some quantity of fluid from the portion of the fluid container; and illuminating at least the portion of the fluid container with light, the light passing through the photopermeable main body portion of the displacement device.

BRIEF DESCRIPTION OF THE DRAWINGS

Illustrative and presently preferred embodiments of the invention are illustrated in the drawings, in which.

DETAILED DESCRIPTION

Figure 1:
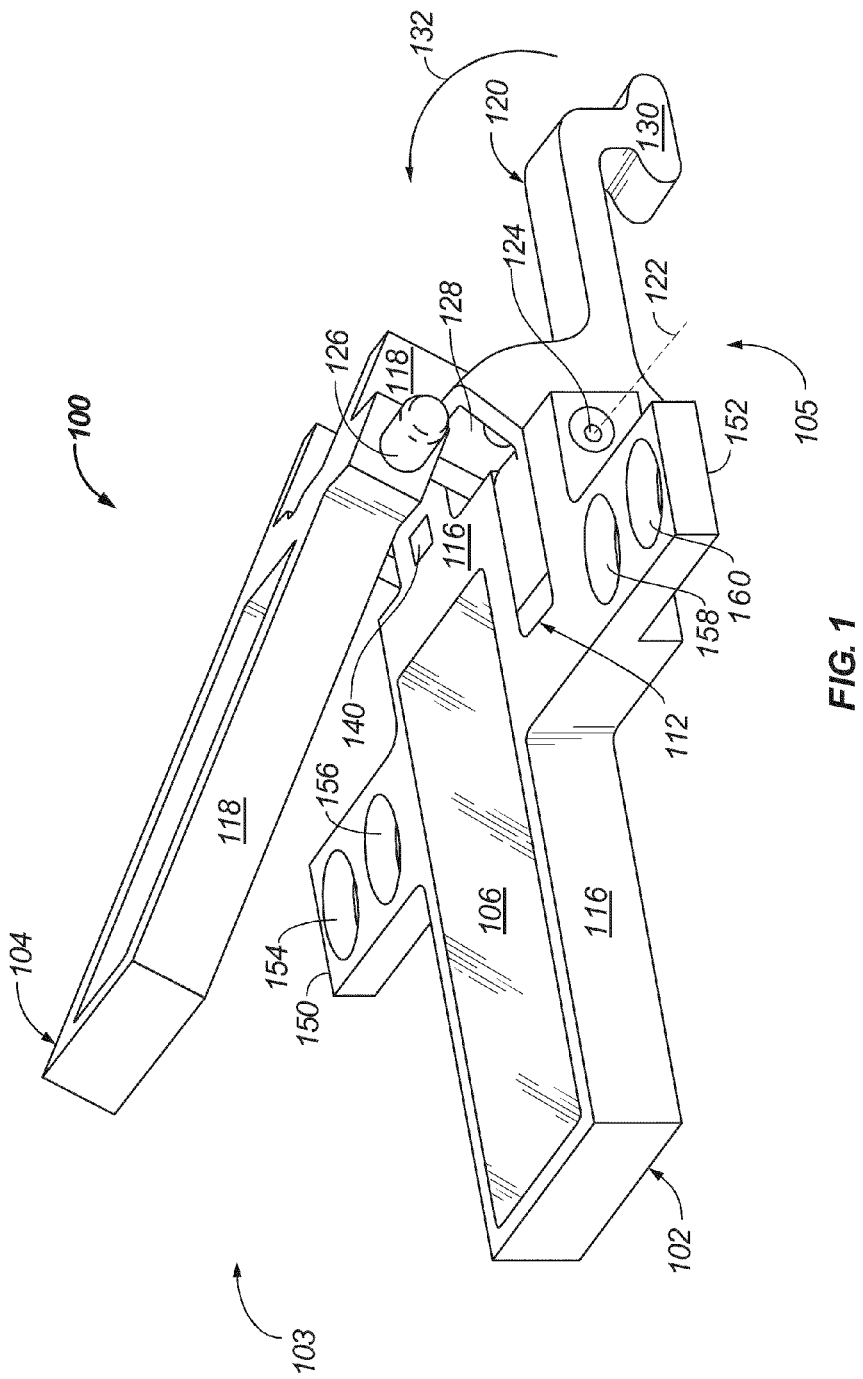
FIG. 1 is a perspective view of a first embodiment of a clamp having lower and upper jaws in the released position.

A first embodiment of a clamp 100 is shown in FIG. 1 and may comprise a lower jaw 102 and an upper jaw 104. The lower jaw 102 of clamp 100 may comprise a photopermeable main body portion 106 and may be coupled to the upper jaw 104. Lower and upper jaws 102, 104 may comprise a rigid metallic material, such as aluminum, for example, and photopermeable main body portion 106 may comprise a transparent material, such as quartz, for example. Additionally, clamp 100 may further comprise a lock member 120 coupled to lower jaw 102. Lock member 120 may also comprise a rigid metallic material, such as aluminum, for example.

Figure 2:
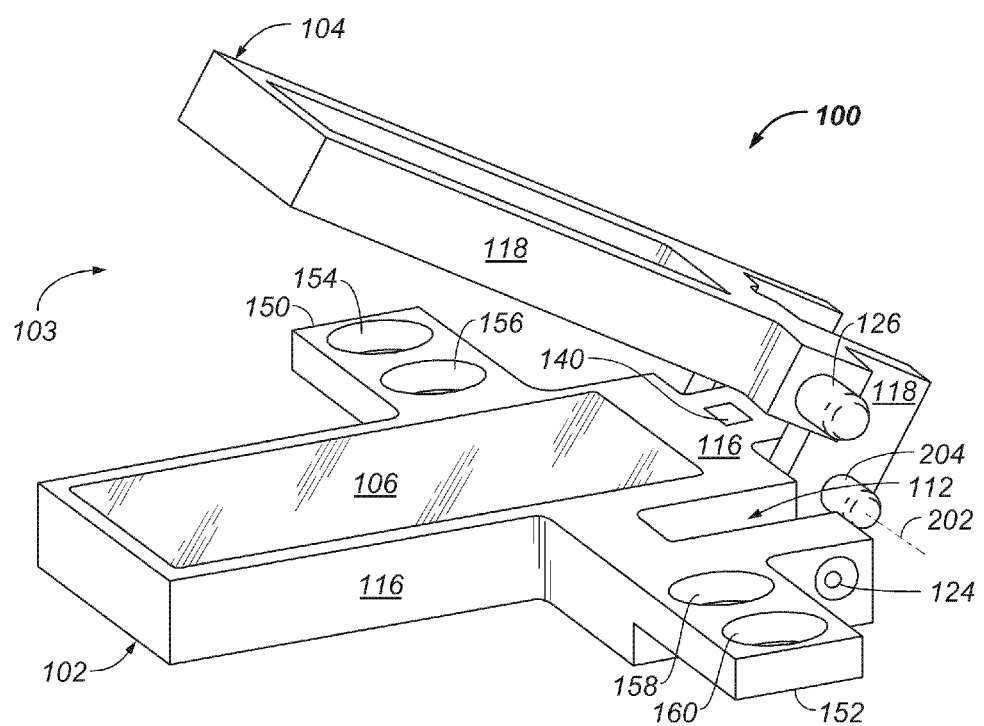
FIG. 2 is a perspective view of the clamp of FIG. 1 having lower and upper jaws in the released position.
Figure 3:
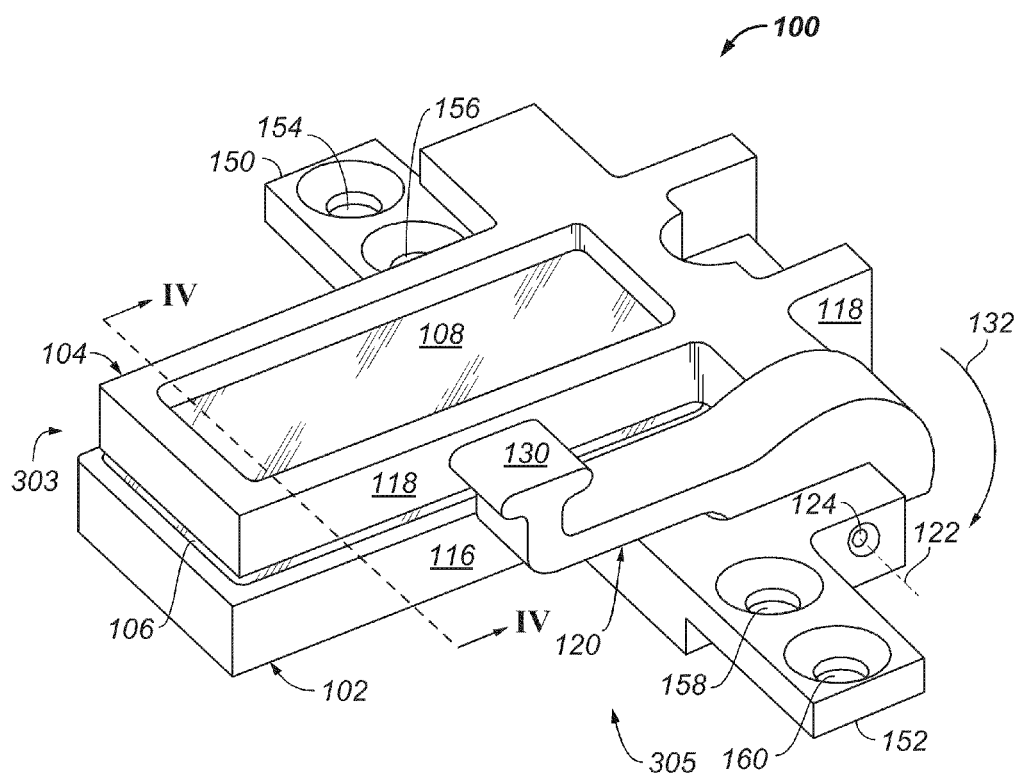
FIG. 3 is a perspective view of the clamp of FIG. 1 having lower and upper jaws in the clamped position.

In exemplary operation, the lower and upper jaws 102, 104 may be operatively associated so that they may be moved between a released position 103 (shown in FIGS. 1 & 2) and a clamped position 303 (shown in FIG. 3). If clamp 100 further comprises lock member 120, lock member 120 may be operatively associated with the lower and upper jaws 102, 104 and may be moved between an unlocked position 105 (shown in FIG. 1) and a locked position 305 (shown in FIG. 3). Lock member 120 may be operated to move at least one of the lower and upper jaws 102, 104 toward clamped position 303 (shown in FIG. 3) as lock member 120 is moved toward locked position 305 (shown in FIG. 3).

Figure 6:
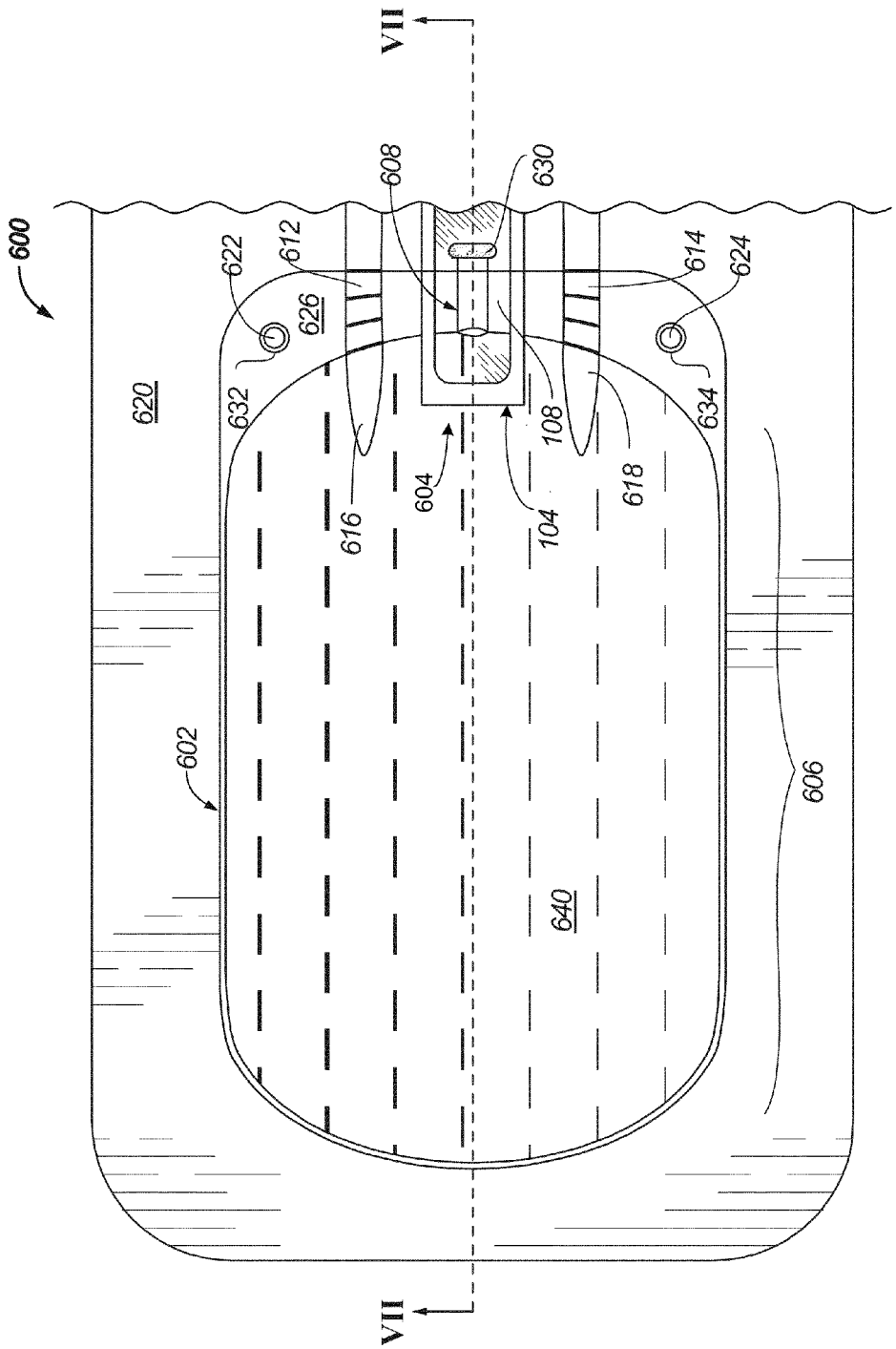
FIG. 6 is a plan view of a portion of a clamp positioned to clamp a portion of a fluid container.
Figure 7:
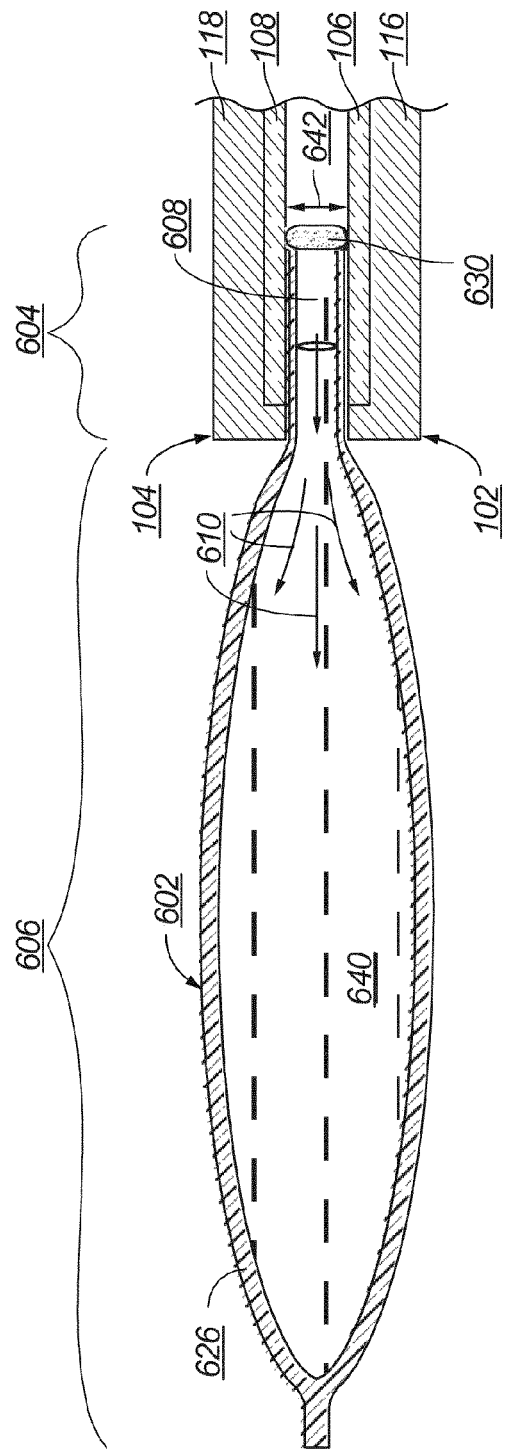
FIG. 7 is a cross-sectional view in elevation taken along the lines 7-7 of FIG. 6.

One exemplary use for clamp 100 is shown in FIGS. 6 & 7. Lower and/or upper jaw(s) 102, 104 of clamp 100 may be operated to clamp a portion 604 of a fluid container 602 therebetween. Clamp 100 may be used to clamp portions of fluid containers, such as polymeric bags and other similar containers, such as those used for storing blood and blood components, for example. Clamp 100 may be operated to displace fluid 640 from a clamped region 604 of the fluid container 602, when at least one of the lower and upper jaws 102, 104 are in clamped position 303 (best shown in FIG. 3). In another embodiment, clamp 100 may be operated to prevent fluid 640 from entering a clamped region (such as clamped region 604).

In one exemplary use, clamp 100 may provide several important advantages for inactivating pathogens within a clamped portion 604 of a fluid container 602, such as within a port path 608 of fluid container 602. Specifically, clamp 100 may displace some amount of fluid 640 from clamped region 604 and create a minimized fluid depth 642 (best shown in FIG. 7) within the clamped region 604 sufficient to allow activation of photosensitizer molecules via photoradiation (i.e. inactivation of pathogens) within clamped region 604 of fluid container 602. Creating a minimized fluid depth 642 within a clamped region 604 flattens the clamped region 604, leaving a thinner layer of fluid therein, so that photoradiation of the clamped region 604 can be done with a lower energy of light, increasing energy per unit of volume.

Having generally described one embodiment of clamp 100 and how it may be operated to clamp a portion 604 of a fluid container 602, as well as some of its features and advantages, several different embodiments will now be described in detail. The structural features of different embodiments of clamps will first be described herein, followed by exemplary operation of those clamps.

The lower and upper jaws 102, 104 may be constructed in a number of different ways and may comprise any number of different sizes and shapes, some of which will be described herein. Additionally, lower and upper jaws 102, 104 may or may not be comprised of similar materials, having similar sizes and shapes, but are shown in FIGS. 1-3 as similar only for simplicity of illustration herein. Lower and upper jaws 102, 104 will now be described in detail, respectively.

In one exemplary embodiment, as shown in FIG. 1, lower jaw 102 may comprise a rigid frame 116 having an opening therein. The opening within frame 116 may be sized to receive a photopermeable main body portion 106, which will be described in more detail below. Frame 116 of the lower jaw 102 may comprise any suitably rigid material, such as aluminum or steel, for example. Frame 116 of lower jaw 102 may have an approximately rectangular shape, as shown in FIG. 1, and may have an elongated end portion (also shown as 116 in FIG. 1), which may be used to couple lower jaw 102 to upper jaw 104, as will be described in more detail below.

Lower jaw 102 may further comprise a slot 112, mounting tabs 150, 152, holes 154 & 156, 158 & 160, and a sensor 140, as shown in FIG. 1. Lower jaw 102 may have a slot 112 sized for receiving a lock member 120, which will be described in more detail below. Lower jaw 102 may also comprise mounting tabs 150, 152 for coupling the lower jaw 102 with a work surface (not shown). Additionally, lower jaw 102 may also comprise holes 154 & 156, 158 & 160 to allow the lower jaw 102 to be secured to a predetermined location on a work surface. In one exemplary embodiment, as shown in FIGS. 1-3, the holes 154 & 156, 158 & 160 may be positioned within the mounting tabs 150, 152.

Lower jaw 102 may further comprise a sensor 140, which may comprise any of a wide range of devices now known in the art or that may be developed in the future that are or will be suitable for use in this particular application. Consequently, the present invention should not be regarded as limited to any particular type of sensor 140. However, by way of example, in one embodiment, sensor 140 may comprise an electrical switch that is closed when the lower and upper jaws 102, 104 are in the clamped position 303 (shown in FIG. 3). In another exemplary embodiment, sensor 140 may comprise any type of mechanical sensor which senses when the lower and upper jaws 102, 104 are in the clamped position 303.

With reference now to upper jaw 104, upper jaw 104 may also comprise a rigid frame 118 having an opening therein. The opening may be sized to receive a photopermeable main body portion 108, which will be described in more detail below. Frame 118 of the upper jaw 104 may comprise any suitably rigid material, such as aluminum or steel, for example. Frame 118 of upper jaw 104 may also have an approximately rectangular shape, as shown in FIGS. 1 & 3, and may or may not have a size and shape approximately equal to those of lower jaw 102.

Upper jaw 104 may also comprise an elongated end portion (also shown as 118 in FIGS. 1 & 3). Elongated end portion 118 may further comprise an angular portion (also shown as 118, best shown in FIG. 1) which may be used to couple upper jaw 104 to lower jaw 102. Upper jaw 104 may also comprise a rigid pin 126 protruding from one of the sides of frame 118, as shown in FIG. 1. Pin 126 is positioned on upper jaw 104 for mating with lock member 120, as will be described in further detail below.

Lower and upper jaws 102, 104 may both comprise openings sized to receive rigid photopermeable main body portions 106, 108 therein. In one embodiment, photopermeable main body portions 106, 108 may be suitably rigid to clamp an object securely therebetween. The photopermeable main body portions 106, 108 may comprise any suitable photopermeable material which is adequately transparent to a desired type of photoradiation, illumination, or light.

Exemplary photopermeable materials for use as photopermeable main body portions 106, 108 may include, but are not limited to, quartz, glass, polycarbonate, polystyrene, polyvinyl chloride, polyolefin, or any other rigid transparent material. In one exemplary embodiment, if photoradiation at ultraviolet wavelengths is desired, it will be important that the photopermeable main body portions 106, 108 be comprised of a photopermeable material which is suitably transparent to ultraviolet wavelengths of light.

In another exemplary embodiment, only one of the lower and upper jaws 102, 104 may comprise a photopermeable body portion 106, 108. For example, in some instances, it may be desirable or necessary to only illuminate the object clamped between the lower and upper jaws 102, 104 from one side (i.e. either through photopermeable main body portion 106 or 108). In this exemplary embodiment, if illumination is desired or necessary from only one side, then only one of the lower and upper jaws 102, 104 may comprise a photopermeable main body portion 106 and/or 108.

Depending upon the use and design of lower and upper jaws 102, 104, the lower and upper jaws 102, 104 may optionally be constructed entirely of the photopermeable material itself. Alternatively, the photopermeable material may comprise only a smaller portion, such as a window area, of the lower and/or upper jaws 102, 104. In yet another embodiment, the frames 116, 118 of the lower and upper jaws 102, 104 may surround or enclose only a few sides (i.e. less than all sides) of the photopermeable main body portions 106, 108.

Figure 4:
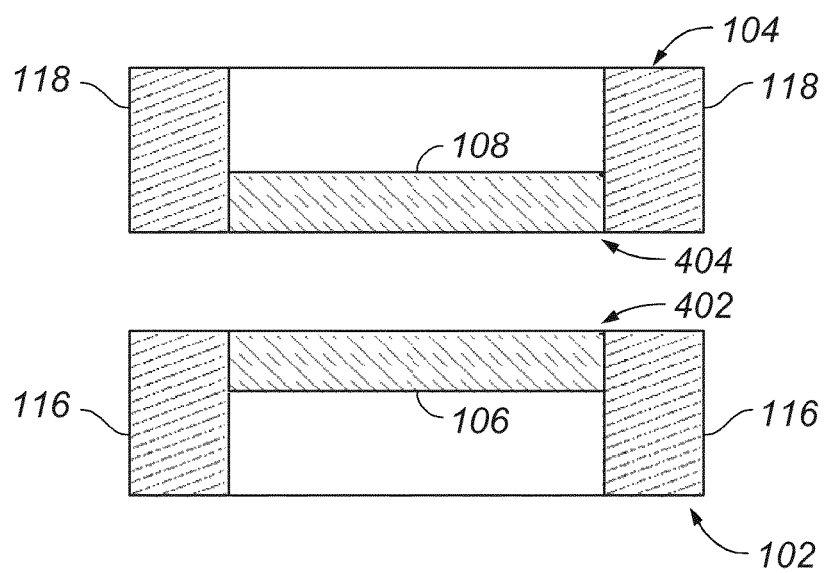
FIG. 4 is a cross-sectional view in elevation taken along the lines 4-4 of FIG. 3.

With reference now to FIG. 4, photopermeable main body portions 106, 108 are positioned within the frames 116, 118, such that each of the photopermeable main body portions 106, 108 are flush within the frames 116, 118 of the jaws 102, 104 along the clamping surfaces 402, 404, which are the surfaces which will clamp an object therebetween. Positioning the frames 116, 118 and the photopermeable main body portions 106, 108 flush together along one surface results in smooth uniform clamping surfaces 402, 404. Clamping surfaces 402, 404 securely and uniformly clamp an object therebetween without undesirable gaps or pockets of air forming between clamping surfaces 402, 404 and an object clamped therebetween (e.g. improving overall clamp operation).

As shown in FIG. 4, the frames 116, 118 and the photopermeable main body portions 106, 108 may have different depths or thicknesses, but are still positioned to be flush together along at least one surface, such as along clamping surfaces 402, 404. Specifically, photopermeable main body portion 106 is positioned within the frame 116 of the lower jaw 102, such that the frame 116 and the photopermeable main body portion 106 together form flush clamping surface 402, resulting in a smooth surface for clamping an object. Similarly, photopermeable main body portion 108 is positioned within the frame 118 of the upper jaw 104, such that the frame 118 and the photopermeable main body portion 108 together form flush clamping surface 404.

As shown in FIG. 1, clamp 100 may further comprise a lock member 120. Lock member 120 may be mounted to the lower or upper jaws 102, 104, and is shown in FIGS. 1 & 3, as being mounted to the lower jaw 102, for example. In the exemplary embodiment shown in FIGS. 1 & 2, lock member 120 may be mounted to lower jaw 102 within slot 112 within the frame 116 of lower jaw 102.

Figure 5:
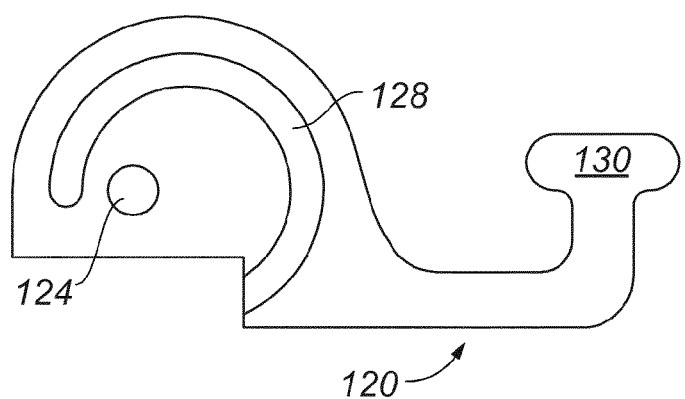
FIG. 5 is a side view in elevation of a first embodiment of a lock member.

With reference now to FIG. 5, lock member 120 may generally comprise an elongated arm-shaped member 120 comprised of any suitable material, such as aluminum or steel, for example. Lock member 120 may further comprise an end portion, such as handle 130, which may be easily grasped by a user or operator when operating lock member 120.

Lock member 120 may further comprise a slot 128 (shown in FIGS. 1 & 5) sized for receiving pin 126 on upper jaw 104, as will be described in more detail below. Slot 128 may comprise a curved or arcuate slot having a generally circular curvature, as shown in FIG. 5. Lock member 120 may further comprise an opening 124 along axis 122 for coupling lock member 120 with the frame 116 of the lower jaw 102. As shown in FIG. 5, opening 124 (along axis 122) may be off-center in relationship to slot 128. Specifically, arcuate slot 128 may comprise a slot having a generally circular curvature having a center of curvature which is displaced from the opening 124 (i.e. axis 122).

As shown in FIGS. 1-3, the lower and upper jaws 102, 104 may be operatively associated so that at least one of the lower and upper jaws 102, 104 may be moved between a clamped position 303 (shown in FIG. 3) and a released position 103 (shown in FIGS. 1 & 2). The lower and upper jaws 102, 104 may be operably associated in any number of ways, such as by mechanical coupling, for example, as will be known by those of ordinary skill in the art after having become familiar with the teachings provided herein.

In one exemplary embodiment, as best shown in FIG. 2, the lower and upper jaws 102, 104 may be coupled together along end portions of frames 116, 118. The end portions of the frames 116, 118 may be pivotally coupled together, such as along a pivot axis 202. The lower and upper jaws 102, 104 may be secured together along pivot axis 202 by a pin 204 such that at least one of the jaws may be moved between a clamped position 303 (FIG. 3) and a released position 103 (FIG. 1). The pivotal coupling of lower and upper jaws 102, 104 along pivot axis 202 with pin 204 is one means for coupling the lower and upper jaws 102, 104 such that at least one of the jaws 102, 104 may be moved between a clamped position 303 (FIG. 3) and a released position 103 (FIGS. 1 & 2).

In one exemplary embodiment, as shown in FIG. 1, lower jaw 102 may remain stationary while upper jaw 104 may be drawn toward lower jaw 102 and toward clamped position 303 (FIG. 3). Alternatively, upper jaw 104 may remain stationary while lower jaw 102 may be drawn toward upper jaw 104 and toward clamped position 303 (FIG. 3). In yet another embodiment, both the lower and upper jaws 102, 104 may be moveable with respect to one another and both jaws 102, 104 may be moved together toward clamped position 303 (FIG. 3).

In an alternative embodiment, the lower and upper jaws 102, 104 may still be operatively associated with one another, but one or both of the lower and upper jaws 102, 104 may be designed to be integral with a platen or work surface (not shown). Clamp 100 is shown in FIG. 2 without lock member 120 for purposes of clearly illustrating an exemplary embodiment of coupling the lower and upper jaws 102, 104, and clamp 100 (of FIG. 2) may also comprise lock member 120, as shown in FIG. 1.

As shown in FIGS. 2 & 3, the lower and upper jaws 102, 104 may be pivotally coupled together along axis 202 such that the photopermeable main body portions 106, 108 are aligned when the lower and upper jaws 102, 104 are in the clamped position 303 (FIG. 3). Aligning the photopermeable main body portions 106, 108 allows an object clamped therebetween to be reached by some wavelengths of light from both above and below the clamp 100 via the photopermeable main body portions 106, 108. Thus, the photopermeable main body portions 106, 108 are critical for allowing at least some wavelengths of light to reach the object clamped therebetween, as will be described in more detail below.

With reference now to FIGS. 1 & 3, lock member 120 may be mounted to lower jaw 102 within slot 112 so that it may be moved in the direction indicated by arrow 132 between a locked position 305 (shown in FIG. 3) and an unlocked position 105 (shown in FIG. 1). Lock member 120 may be mounted to the lower jaw 102 such that it engages the upper jaw 104 as it is moved from the unlocked position 105 to the locked position 305. As shown in FIG. 1, for example, lock member 120 may be mounted to lower jaw 102 within slot 112 within frame 116 of lower jaw 102. Lock member 120 is one means for moving at least one of the lower and upper jaws 102, 104 between a clamped position 303 (FIG. 3) and a released position 103 (FIG. 1).

In one exemplary embodiment, lock member 120 may be pivotally mounted to lower jaw 102, such as along pivot axis 122, by inserting a pin or other retaining mechanism into opening 124. In this embodiment, lock member 120 may be mounted to lower jaw 102 for rotation about pivot axis 122 so that it may be pivoted between an unlocked position 105 (FIG. 1) and a locked position 305 (FIG. 3) in the direction indicated by arrow 132.

In one exemplary embodiment, as shown in FIGS. 1 & 3, lock member 120 may comprise a slot 128 which engages pin 126 on the upper jaw 104, as lock member 120 is pivoted (in the direction indicated by arrow 132) from the unlocked position 105 (FIG. 1) to the locked position 305 (FIG. 3). In one embodiment, the engagement of pin 126 within slot 128 may cause lock member 120 to draw the upper jaw 104 toward the lower jaw 102 and toward the clamped position 303 (FIG. 3) as the lock member 120 is pivoted toward the locked position 305 (FIG. 3) in the direction indicated by arrow 132.

In an alternative embodiment (shown best in FIGS. 8 & 9), the engagement of pin 126 within slot 128 may retain lock member 120 in the locked position 305 and may hold the lower and upper jaws 102, 104 in the clamped position 305 (FIG. 3). In one embodiment (shown best in FIG. 14), the slot 128/1428 may have a crest 1429 therein to more securely retain the lock member 120/1320 in the locked position. In another alternative embodiment (not shown), lock member 120 may be designed to open at least one, or both, of the lower and upper jaws 102, 104 toward the released position 103 (FIG. 1) as the lock member 120 is pivoted toward the locked position 305 (FIG. 3).

As shown in FIG. 5, the slot 128 of lock member 120 may comprise an arcuate slot 128 curved so that the engagement of the pin 126 in the arcuate slot 128 slideably draws the upper jaw 104 closer to the lower jaw 102 as the lock member 120 pivots toward the locked position 305 (FIG. 3) in the direction indicated by arrow 132. Slot 128 may have a generally circular curvature having a center of curvature that is displaced from the pivot axis 122, resulting in eccentric clamping between lower and upper jaws 102, 104.

An exemplary use of clamp 100 is shown in FIG. 6, wherein an exemplary clamp assembly 600 may comprise a fluid container 602 having fluid 640 therein, a lower jaw 102, and an upper jaw 104 (shown in FIG. 7). As shown in FIG. 6, and described above, the lower jaw 102 may comprise a photopermeable main body portion 106 and the upper jaw 104 may be operatively associated with the lower jaw 102 so that at least one of the lower and/or upper jaw(s) 102, 104 may be moved together to clamp a portion 604 of a fluid container 602 therebetween.

The positioning of the photopermeable main body portions 106, 108 of the clamp 100 with respect to a portion of the fluid container to be clamped therebetween (such as portion 604) is important for allowing some wavelengths of light to reach the clamped portion 604 of the fluid container 602, as shown in FIG. 6. In the embodiment shown in FIG. 6, fluid container 602 may be positioned on a platen or work surface 620 and may be positioned at a predetermined location on the platen 620 by aligning pins 622, 624 on the platen 620 with holes 632, 634 provided in the welded end portion 626 of fluid container 602. In one embodiment, alignment of the holes 632, 634 in the fluid container 602 with pins 622, 624 on the work surface 620 may also align a predetermined portion (such as portion(s) 604 and/or 608) of the fluid container 602 with the photopermeable main body portions 106, 108 of the clamp 100.

In one exemplary embodiment it may be desirable to clamp a predetermined portion of fluid container 602, such as inlet port path 608, such that the inlet port path 608 is aligned within the photopermeable main body portions 106, 108. In this embodiment, alignment of the fluid container 602 on work surface 620 may also align the inlet port path 608 of the fluid container 602 with the photopermeable main body portions 106, 108 of clamp 100. In one exemplary embodiment, fluid container 602 may be carefully aligned with clamp 100 to clamp only a minimal portion of the fluid container 602, such as only the inlet port path 608, to avoid over-exposing the remainder of the clamped portion 604 of the fluid container 602 to photoradiation (which may destroy biological activity of the fluid 640).

Fluid containers commonly comprise multiple port paths 608, 612, 614 for accessing the interior of the fluid container 602. As shown in FIG. 6, for example, fluid container 602 may comprise one inlet port path 608 and two outlet port paths 612, 614. Sometimes stagnant fluid contained within these port paths 608, 612, 614 may pose several problems during pathogen inactivation. First, the stagnant fluid may not be adequately mixed with photosensitizer for pathogen inactivation to occur. Second, the stagnant fluid within the port paths 608, 612, 614 may be of a depth and/or volume which is too great for sufficient photoradiation (i.e. pathogen inactivation) to occur. Consequently, fluid trapped within these port paths 608, 612, 614 may still contain pathogens after the inactivation process is completed, and these pathogens may then reenter the otherwise inactivated fluid 640 reinfecting the fluid 640 and posing health risks.

Typically, inlet port path 608 may be used for adding blood and/or other fluids, such as photosensitizing agents, to fluid container 602, while outlet port paths 612, 614 may be used for removing fluids from fluid container 602. After fluids 640 are added to fluid container 602, inlet port path 608 may be sealed off at end portion 630, such as by heat welding, for example, resulting in welded end portion 630. It is known in the art to seal off the inlet ports and/or outlet ports of fluid containers during use, such as is done by using electromagnetic or radio frequency (RF) energy as disclosed in U.S. Pat. No. 5,685,875 to Hlavinka, which is herein incorporated by reference for all that it discloses. Various sorts of electromagnetic energies may be applied to create such seals, however, the choice of materials used in the inlet ports and/or outlet ports 608, 612, 614 is related to the chosen sealing method.

The outlet port paths 612, 614 may be used by an end-user of fluid container 602 wishing to remove the fluid 640 from the fluid container 602. The user may remove fluid 640 by breaking off break-away end portions 616, 618, commonly known as frangibles 616, 618, to allow fluid 640 to flow out (e.g. usually with gravity assistance) of the outlet port paths 612, 614. In an embodiment having frangibles 616, 618 covering the outlet port paths 612, 614, stagnant fluid within the outlet port paths 612, 614 may not be a problem during pathogen inactivation because the frangibles 616, 618 may cover the outlet port paths 612, 614 to prevent this problem.

However, in other embodiments, such as where frangibles 616, 618 are absent, positioned outside the edge of the fluid container 602, or are flexibly crushable (i.e. deformable), it may be desirable to clamp the outlet port paths 612, 614 as well as the inlet port path 608. Thus, clamp 100 may be similarly used to clamp outlet port paths 612, 614 as well as inlet port path 608. In yet another embodiment, clamp 100 may be larger and may be positioned to clamp all of the port paths 608, 612, 614 of a fluid container 602. In yet another embodiment, clamp 100 may be used to clamp an entirely different portion of a fluid container 602, such as a portion or area of fluid container 602 which does not contain any port paths, for example.

With reference now to FIGS. 6 & 7, as the lower and upper jaws 102, 104 are clamped together, the clamped region 604 will be crushed. FIG. 7 illustrates the lower and upper jaws 102, 104 just before they crush and deform the clamped region 604. Thus, FIG. 7 does not show clamped region 604 as being deformed, but as the lower and upper jaws 102, 104 are further clamped together, the clamped region 604 would be crushed and would be deformed (not shown for simplicity of illustration).

With continuing reference to FIGS. 6 & 7, as the lower and upper jaws 102, 104 are clamped together, fluid 640 within inlet port path 608 will be forced out into the unclamped region 606 of the fluid container 602, in the direction indicated by arrows 610 (shown in FIG. 7). Any fluid 640 remaining within the inlet port path 608 may be minimal enough in depth 642 to be effectively photoradiated to activate photosensitizer molecules within inlet port path 608 (i.e. to inactivate pathogens within the inlet port path 608). When clamp 100 crushes and deforms inlet port path 608 it may also flatten the inlet port path 608, resulting in a more uniform and/or flat surface having a thinner layer of fluid 640 therein for photoradiation, which may increase energy per until volume during photoradiation, increasing ability to activate photosensitizer molecules therein (i.e. increasing pathogen inactivation success). In yet another embodiment, clamp 100 may be operated to prevent fluid 640 from entering clamped region 604 (in the opposite direction of arrows 610).

The portion of clamp 100 illustrated in FIG. 6 is shown without a lock member 120, pivot axis and/or pin 202/204, or mounting tabs 150, 152 for simplicity of illustration herein, but clamp 100 may also comprise the lock member 120, pivot axis and/or pin 202/204, and mounting tabs 150, 152, as previously described above. Additionally, in some exemplary embodiments, the entire fluid container 602 may be pressed between two additional surfaces (not shown) during a pathogen inactivation process; however this is also not illustrated in FIG. 6 for simplicity of illustration.

Figure 12:
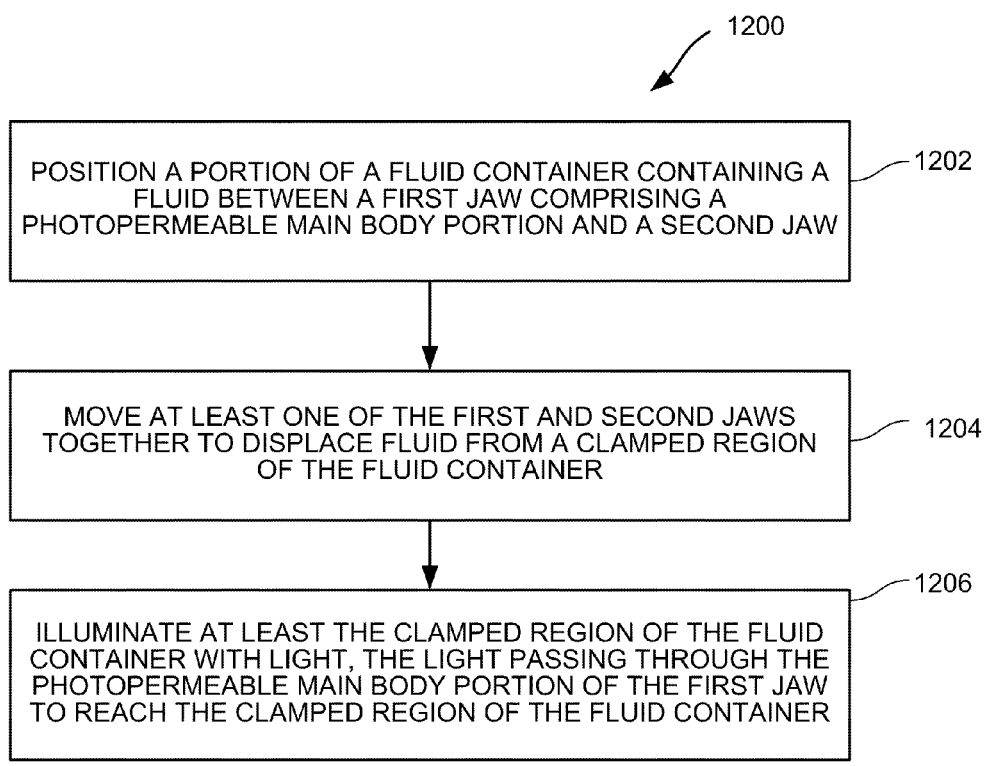
FIG. 12 is a flow chart of a method of operating a clamp to clamp a portion of a fluid container.

In one exemplary embodiment a method 1200 for operating a clamp is disclosed and shown in FIG. 12. The clamp operation 1200 begins by positioning 1202 a portion 604 of a fluid container 602, having a fluid 640 therein, between a lower jaw 102 comprising a photopermeable main body portion 106 and an upper jaw 104. As described above, if photoradiation from both above and below clamp 100 is desirable, then both the lower and upper jaws 102, 104 may comprise the photopermeable main body portions 106, 108 and these portions may be aligned to position the clamped region 604 therebetween. Alternatively, if photoradiation from only one side of clamp 100 is desired, then only one of the jaws 102, 104 needs to have a photopermeable main body portion 106 or 108.

After positioning 1202 the fluid container 602, at least one of the lower and/or upper jaw(s) 102, 104 are moved 1204 together to displace fluid 640 from a clamped region 604 of the fluid container 602. In one exemplary embodiment, the clamped region 604 of fluid container 602 may comprise an inlet port path 608 and an unclamped region 606 of the fluid container 602 may comprise the main body portion 606 of the fluid container 602. In this arrangement, clamping the inlet port path 608 will squeeze some amount of fluid 640 out of the inlet port path 608 and into the unclamped portion 606 of the fluid container 602, in the direction indicated by arrows 610 (shown in FIG. 7).

After moving the lower and upper jaws 102, 104 together, at least the clamped region 604 of the fluid container 602 is illuminated 1206 with light. In one exemplary embodiment, the entire fluid container 602 may be illuminated and illumination may comprise photoradiating the fluid container 602 to activate a photosensitizing agent to inactivate pathogens. In this exemplary embodiment, the light or photoradiation may pass through the photopermeable main body portion 108 of the upper jaw 104 to photoradiate the inlet port path 608 within the clamped region 604 of the fluid container 602.

The specific wavelength of light used during photoradiation may depend on the specific photosensitizing agent selected, as will be known by those of ordinary skill in the art after having become familiar with the teachings herein. The light or photoradiation may be provided by a light source (not shown), which may provide light having wavelengths in the visible range, the ultraviolet range, or a mixture of light in both the visable and ultraviolet ranges. In one exemplary embodiment, ultraviolet wavelengths of light may be used, more specifically; UVB wavelengths of light may be used. In some embodiments, wavelengths of light of approximately 450 nm may be used for photoradiating platelets or plasma, for example.

Figure 15:
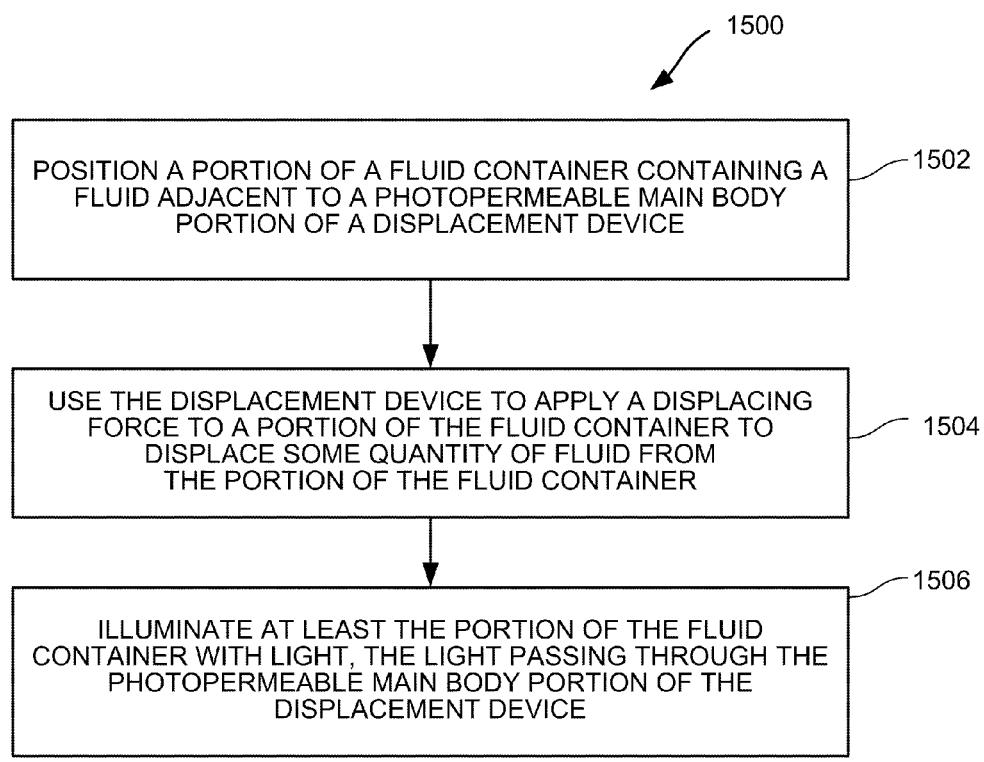
FIG. 15 is a flow chart of a method of displacing fluid from a portion of a fluid container.

In another exemplary embodiment a method 1500 for displacing fluid from a portion of a fluid container is disclosed and shown in FIG. 15. The method 1500 of displacing fluid begins by positioning 1502 a portion of a fluid container containing a fluid adjacent to a photopermeable main body portion of a displacement device. The displacement device may generally comprise a clamp 100 or may comprise a device such as a flexible or pressure-driven device, such as air-filled bags having photopermeable main body portions therein. In one embodiment a clamp 100 may be operated according to method 1500 using pneumatic pressure to operate clamping jaws 102, 104, for example. In another embodiment, only one of the clamping jaws 102, 104 may be operated via pneumatic pressure and the other jaw 102, 104 may remain stationary.

After positioning 1502 a portion of a fluid container, the displacement device may be used 1504 to apply a displacing force to a portion of the fluid container to displace some quantity of fluid from the portion of the fluid container. After displacing some quantity of fluid from the portion of the fluid container, the portion of the fluid container may be illuminated 1506 with light. The light passing through the photopermeable main body portion of the displacement device to illuminate 1506 at least the portion of the fluid container.

Figure 8:
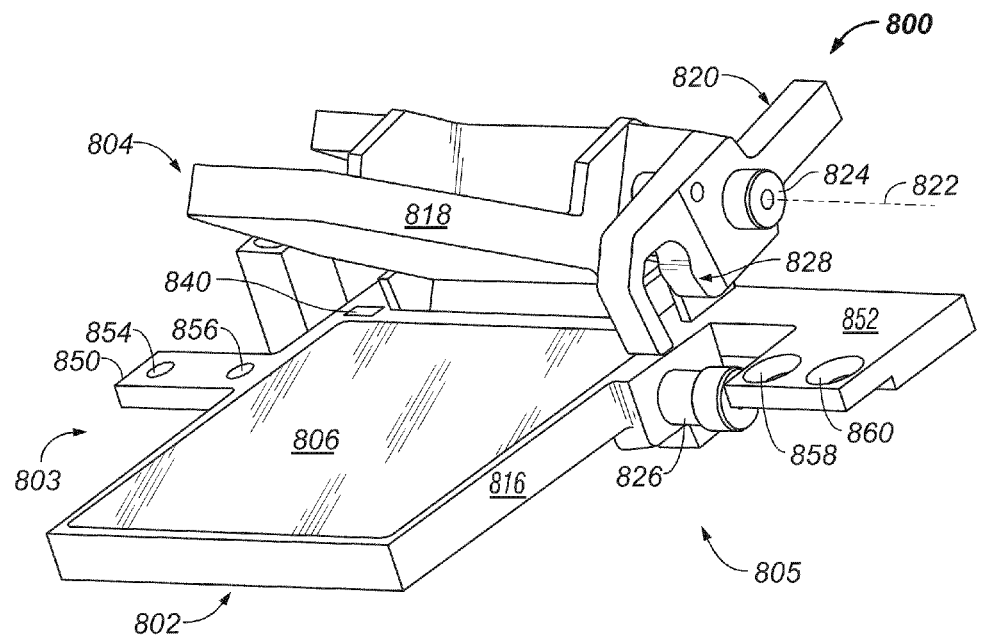
FIG. 8 is a perspective view of a second embodiment of a clamp having lower and upper jaws in the released position.
Figure 9:
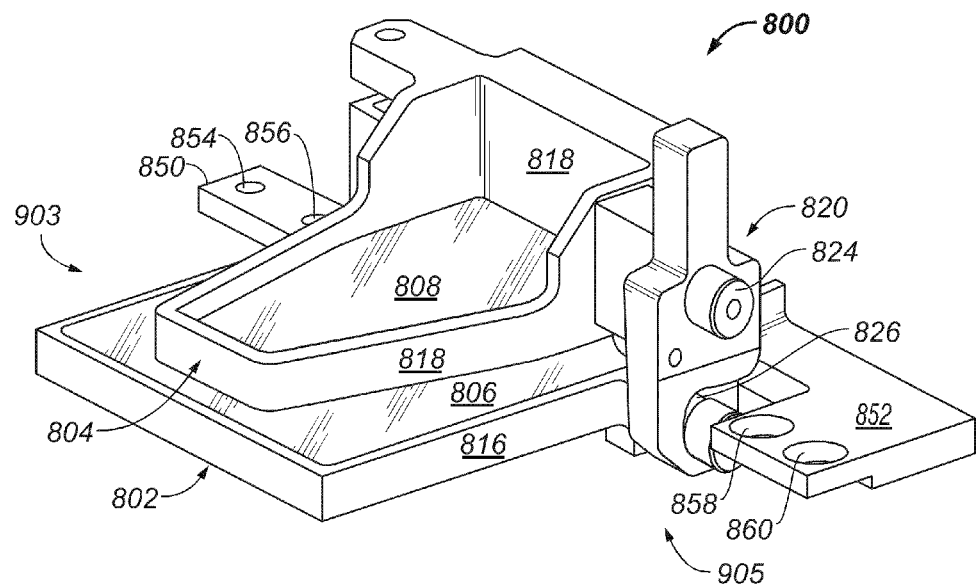
FIG. 9 is a perspective view of the clamp of FIG. 8 having lower and upper jaws in the clamped position.

Another exemplary embodiment of a clamp 800 is shown in FIGS. 8 & 9. Clamp 800 may comprise lower and upper jaws 802, 804 having photopermeable main body portions 806, 808 sized to be received by frames 816, 818, as described above. FIGS. 8 & 9 have numbering corresponding to FIGS. 1-3, previously described above.

Lower jaw 802 may have an approximately square shape while upper jaw 804 may have an approximately trapezoidal shape. As will be known by those of ordinary skill in the art after having become familiar with the teachings herein, any number of geometric shapes may be used to construct the lower and upper jaws 802, 804. As shown in FIGS. 8 & 9, the lower and upper jaws 102, 104 may have different sizes and shapes, but the photopermeable main body portions 106, 108 may still be aligned in the clamped position 903 to clamp an object or portion of an object therebetween such that the object may be photoradiated while being clamped.

Clamp 800 may further comprise a lock member 820 coupled to upper jaw 804. Lock member 820 may comprise a rigid elongated arm-shaped member having a slot 828 on one end. Lock member 820 may comprise any suitably rigid material, such as aluminum or steel, for example. Slot 828 may be cut into one end of lock member 820 such that lock member 820 forms a hooked-portion on one end. The opposite end of lock member 820 may comprise an elongated portion which may be easily grasped and moved by a user. Clamp 800 may further comprise a sensor 840, mounting tabs 850, 852, and alignment holes 854 & 856, 858 & 860, similar to those described above with respect to FIGS. 1-3.

In one embodiment, as shown in FIGS. 8 & 9, for example, lower and upper jaws 802, 804 may be operatively associated such that at least one of the lower and/or upper jaw(s) 102, 104 may be moved between a clamped position 903 (FIG. 9) and a released position 803 (FIG. 8). Lower and upper jaws 802, 804 may be pivotally coupled along a pivot axis (not shown in FIGS. 8 & 9) such that the lower and upper jaws 802, 804 may be rotated between the clamped position 903 (FIG. 9) and the released position 803 (FIG. 8), as described above with respect to FIGS. 1-3.

As shown in FIGS. 8 & 9, the lock member 820 may be mounted to the upper jaw 804 so that the lock member 820 can be moved between a locked position 905 (FIG. 9) and an unlocked position 805 (FIG. 8). Lock member 820 may be pivotally mounted to upper jaw 804 along pivot axis 822 and coupled to upper jaw 804 via any suitable means, such as by hinge pin 824. The slot 828 of the lock member 820 may be sized to engage a rod or pin 828 on the lower jaw 802 as the lock member 820 is moved from the unlocked position 805 (FIG. 8) to the locked position 905 (FIG. 9). Lock member 820 secures the lower and upper jaws 802, 804 together in the clamped position 903 (FIG. 9). Lock member 820 may comprise one means for moving at least one of the lower and/or upper jaw(s) 802, 804 between a clamped position 903 and a released position 803.

Figure 13:
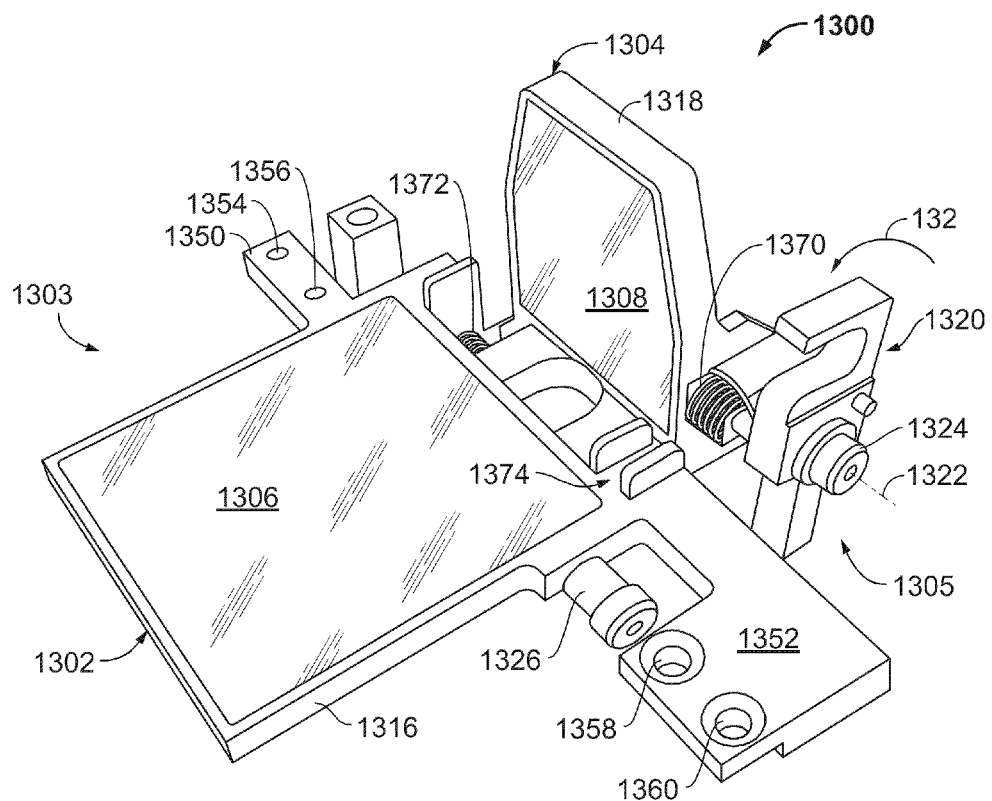
FIG. 13 is a perspective view of a fourth embodiment of a clamp having lower and upper jaws in the released position.
Figure 14:
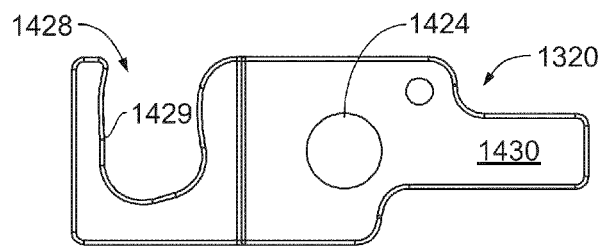
FIG. 14 is a side view in elevation of a second embodiment of a lock member.

Yet another embodiment is shown and described with reference to FIGS. 13 & 14. Clamp 1300 may comprise lower and upper jaws 1302, 1304 having photopermeable main body portions 1306, 1308 sized to be received by frames 1316, 1318, as describe above. FIGS. 13 & 14 have numbering corresponding to FIGS. 1-3 and FIGS. 8 & 9, all previously described in detail above.

As illustrated in FIGS. 13 and 14, a clamp 1300 may be provided with an interlock system (shown generally as 1300) to prevent the lock member 1320 from remaining in the locked position (905 shown in FIG. 9) unless a fluid container 602 is present and properly positioned between the jaws 1302, 1304 of clamp 1300. In one embodiment, interlock system 1300 may comprise a small rib or crest 1429 (best shown in FIG. 14) formed in the slot 1428 of lock member 1320. The rib or crest 1429 is sized and positioned within slot 1428 of lock member 1320 so as to engage a pin 1326, provided on lower jaw 1302, when lock member 1320 is in the locked position (905 shown in FIG. 9).

Interlock system (generally 1300) may also comprise a biasing device or spring 1370 operatively associated with lock member 1320 for biasing lock member 1320 to the unlocked position 1305 (shown in FIG. 13). If a fluid container 602 is absent or not properly positioned between the jaws 1302, 1304 of clamp 1300, the spring 1370 will return lock member 1320 to the unlocked position 1305. Accordingly, interlock system 1300 may provide a more positive indication to a user that the fluid container 602 is absent or not properly positioned between the jaws 1302, 1304 of clamp 1300.

More specifically, if the fluid container 602 is absent or not properly positioned between the jaws 1302, 1304 of clamp 1300, no opposing force (or an insufficient opposing force) will be provided to the jaws 1302, 1304 of clamp 1300 when the lock member 1320 is in the locked position (905 shown in FIG. 9). Thus, the engagement of pin 1326 (on jaw 1302) with the crest 1429 formed in the slot 1428 in the lock member 1320 will be such that the pin 1326 will not provide sufficient opposing force on the crest 1429 to prevent the spring 1370 from returning the lock member 1320 to the unlocked position 1305. That is, in order for lock member 1320 to be returned to the unlocked position 1305, the crest 1429 formed in slot 1428 of lock member 1320 will exert a force on pin 1326 that will urge at least one of the jaw(s) 1302, 1304 of clamp 1300 together. Thus, if the fluid container 602 is absent or not properly positioned between the jaws 1302, 1304, no opposing force, or an insufficient opposing force, will be provided on the jaws 1302, 1304, thereby allowing the spring 1370 to return lock member 1320 to the unlocked position 1305.

However, if a fluid container 602 is properly positioned between jaws 1302, 1304 of clamp 1300, the compliant material of the fluid container 602 will oppose the further closing of the jaws 1302, 1304, thereby preventing pin 1326 from being moved to the degree necessary to clear the crest 1429 of the slot 1428 and preventing spring 1370 from returning lock member 1320 to the unlocked position 1305. Stated another way, if the fluid container 602 is properly positioned between the jaws 1302, 1304 of clamp 1300, the spring 1370 will not be able to overcome the cooperative engagement of the pin 1326 and the crest 1429 and lock member 1320 will remain in the locked position (905 shown in FIG. 9).

The interlock system (generally 1300) may be provided with additional components if necessary or desired to enhance operation. For example, in one embodiment, interlock system (generally 1300) may also comprise a biasing device or spring 1372, operatively associated with the jaws 1302, 1304 of clamp 1300. The spring 1372 may be arranged to bias the jaws 1302, 1304 of clamp 1300 to the unclamped position 1303. Thus, in an operational situation wherein the interlock system 1300 causes lock member 1320 to be returned to the unlocked position 1305, the spring 1372 will cause the jaws 1302, 1304 to move to the unclamped position 1303.

The unclamping 1303 of jaws 1302, 1304 of clamp 1300 may provide an additional indication to a user that the fluid container 602 is absent or not properly positioned between jaws 1302, 1304 of clamp 1300. If such a biasing device or spring 1372 is provided to bias the jaws 1302, 1304 to the unclamped position 1303, the biasing force should not be so great as to prevent the spring 1372 from returning the lock member 1320 to the unlocked position 1305 if the fluid container 602 is absent or not properly positioned between the jaws 1302, 1304 of clamp 1300, in the manner already described.

Figure 10:
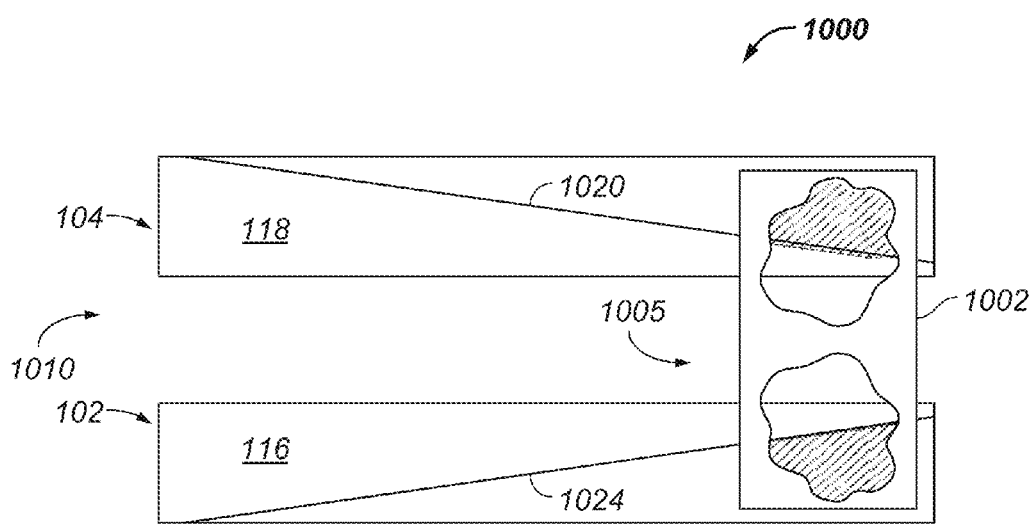
FIG. 10 is a side view in elevation of a third embodiment of a clamp.
Figure 11:
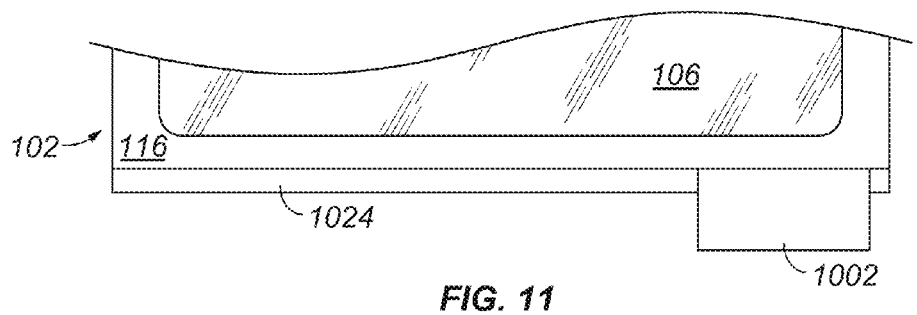
FIG. 11 is a plan view of a portion of the clamp of FIG. 10.

Yet another embodiment is shown and described with regard to FIGS. 10 & 11. Clamp 1000 may comprise lower and upper jaws 102, 104 having frames 116, 118, which may have photopermeable main body portions 102, 104 therein (not shown), as previously described above. Clamp 1000 may further comprise a lock member 1002. Lock member 1002 may generally comprise a rigid rectangular or buckle-shaped mechanism. Lock member 1002 may comprise any suitably rigid material, such as aluminum or steel, and may even comprise a rigid photopermeable material, as described above.

Clamp 1000 may further comprise ramps 1020, 1024 mounted to the sides of the lower and upper jaws 102, 104. The ramps 1020, 1024 may comprise any rigid material, such as aluminum or steel, and may even comprise a rigid photopermeable material, as described above. The ramps 1020, 1024 may provide a slideable means for operating the lock member 1002, to move the lower and upper jaws 102, 104 between a clamped position and a released position 1010.

The lower and upper jaws 102, 104 may be operatively associated with one another so that they may be moved between a clamped position and a released position 1010 (shown in FIG. 10). The lower and upper jaws 102, 104 may be moveable via the lock member 1002. Lock member 1002 may be operated to slideably draw the lower and upper jaws 102, 104 together as the lock member 1002 proceeds up the ramps 1020, 1024 and toward the locked position. Lock member 1002 is shown in FIG. 10 in the unlocked position 1005 with the lower and upper jaws 102, 104 in the unclamped 1010 position. However, as lock member 1002 slides up the ramps 1020, 1024 and toward the locked position, the lower and upper jaws 102, 104 may be slideably drawn together, clamping an object therebetween.

It should be understood that various changes and modifications to the presently preferred embodiments described herein will be apparent to those of ordinary skill in the art after having become familiar with the teachings provided herein. It is foreseeable that the shape and size of the clamps and displacement devices, as well as the number of clamps and displacement devices used on one fluid container, and the positioning of the clamps and displacement devices on the fluid container may be varied. It is also foreseeable that the clamps and displacement devices may be manufactured out of a plurality of different materials having a plurality of different thicknesses, including different photopermeable materials.

Additionally, different applications and intended uses for the clamps and displacement devices disclosed herein are also contemplated. These examples are not meant to be limiting, but rather are exemplary of the modifications that can be made without departing from the spirit and scope of the present invention and without diminishing its attendant advantages.

What is claimed is:

1. A clamp assembly, comprising:
   a fluid container containing a fluid;
   the fluid container comprising
     an inlet port path; and
     a bag main body portion;
   a clamp, the clamp being sized to receive the inlet port path but not the bag main body portion;
   the clamp comprising
     a first jaw having a photopermeable main body portion; and
     a second jaw, said fluid chamber inlet port path being between the first and second jaw, the second jaw being operatively associated with the first jaw so that at least one of the first and second jaws can be moved between a clamped position and a released position with respect to the inlet port path, wherein at least one of the first and second jaws applies a clamping force in the clamped position to the fluid container to displace fluid from the clamped inlet port path to the bag body portion; and wherein the photopermeable main body portion of the first jaw allowing some light to reach the clamped region of the fluid container,
   a lock member mounted to the second jaw so that the lock member can be moved between a locked position and an unlocked position, the lock member engaging the first jaw and holding the first and second jaws in the clamped position when the lock member is in the locked position, and
   an interlock operatively associated with the lock member, the interlock preventing the lock member from remaining in the locked position unless the fluid container is positioned between the first and second jaws.

2. The clamp assembly of claim 1, wherein the second jaw comprises a photopermeable main body portion.

3. The clamp assembly of claim 2, wherein the photopermeable main body portions of the first and second jaws comprise quartz.

4. The clamp assembly of claim 1, wherein the interlock further comprises a spring, the spring biasing the lock member toward the unlocked position.

5. The clamp assembly of claim 4, wherein the lock member defines a slot having a crest therein and wherein the first jaw comprises a pin sized to be received by the slot in the lock member, the slot in the lock member engaging the pin on the first jaw as the lock member is moved toward the locked position, and wherein the crest in the slot retains the lock member in the locked position.

6. The clamp assembly of claim 1, wherein the first and second jaws are pivotally connected together along a pivot axis.

7. The clamp assembly of claim 6, further comprising a lock member mounted to the first jaw so that the lock member can be moved between a locked position and an unlocked position, the lock member engaging the second jaw as the lock member is moved from the unlocked position to the locked position, the lock member drawing the first and second jaws together toward the clamped position as the lock member is moved toward the locked position.

8. The clamp assembly of claim 6, further comprising a lock member mounted to the first jaw so that the lock member can be moved between a locked position and an unlocked position, the lock member engaging the second jaw as the lock member is moved from the unlocked position to the locked position, the lock member drawing the second jaw toward the first jaw as the lock member is moved toward the locked position.

9. The clamp assembly of claim 8, wherein the lock member defines a slot therein and wherein the second jaw comprises a pin sized to be received by the slot in the lock member, the slot in the lock member engaging the pin on the second jaw as the lock member is moved toward the locked position.

10. The clamp assembly of claim 6, further comprising a lock member having a slot therein, wherein the lock member is mounted for rotation about a pivot axis so that the lock member can be pivoted between a locked position and an unlocked position, the slot in the lock member engaging a pin on the second jaw as the lock member is pivoted from the unlock position to the locked position, the lock member drawing the second jaw toward the first jaw and toward the clamped position as the lock member is pivoted toward the locked position.

11. The clamp assembly of claim 10, wherein the slot comprises an arcuate slot curved so that the engagement of the pin in the arcuate slot draws the second jaw closer to the first jaw as the lock member pivots toward the locked position; wherein the arcuate slot has a generally circular curvature having a center of curvature that is displaced from the pivot axis.

12. The clamp assembly of claim 1, wherein the first jaw comprises a frame, the frame sized to receive the photopermeable main body portion.

13. The clamp assembly of claim 1 wherein:
the first jaw comprises:
  a frame, the frame of the first jaw defining an opening therein; and
  the photopermeable main body portion is sized to be received by the opening defined by the frame of the first jaw.

14. The clamp assembly of claim 13 wherein
the second jaw comprises:
  a frame, the frame of the second jaw defining an opening therein; and
  the photopermeable main body portion is sized to be received by the opening defined by the frame of the second jaw.

15. The clamp assembly of claim 14 wherein
the frames of the first and second jaws being pivotally connected together so that at least one of the first and second jaws can be pivoted about a pivot axis between a clamped position and a released position.

16. A clamp assembly of claim 1 further comprising:
a means for moving at least one of the first and second jaws between the clamped position and the released position, wherein the means is operatively associated with at least one of the first and second jaws.

17. A clamp assembly, comprising:
a fluid container containing a fluid;
the fluid container comprising
  an inlet port path; and
  a bag main body portion;
a clamp, the clamp being sized to receive the inlet port path but not the bag main body portion;
the clamp comprising
  a first jaw having a photopermeable main body portion; and
  a second jaw, said fluid chamber inlet port path being between the first and second jaw, the second jaw being operatively associated with the first jaw so that at least one of the first and second jaws can be moved between a clamped position and a released position with respect to the inlet port path, wherein at least one of the first and second jaws applies a clamping force in the clamped position to the fluid container to displace fluid from the clamped inlet port path to the bag body portion; and
  wherein the photopermeable main body portion of the first jaw allowing some light to reach the clamped region of the fluid container, and
a sensor for sensing when at least one of the first and second jaws are in the clamped position.

* * * * *